(12) United States Patent
Kirby et al.

(10) Patent No.: US 8,523,758 B1
(45) Date of Patent: Sep. 3, 2013

(54) SYSTEM AND METHOD OF TREATMENT FOR INSOMNIA AND OCCASIONAL SLEEPLESSNESS

(75) Inventors: Todd Kirby, Spring Church, PA (US); Erik K. Witt, Murrysville, PA (US); Smita Garde, Irvine, CA (US)

(73) Assignee: RIC Investments, LLC, Wilmington, DE (US)

( * ) Notice: Subject to any disclaimer, the term of this patent is extended or adjusted under 35 U.S.C. 154(b) by 1072 days.

(21) Appl. No.: 12/113,916

(22) Filed: May 1, 2008

Related U.S. Application Data

(60) Provisional application No. 60/915,490, filed on May 2, 2007.

(51) Int. Cl.
*A61M 21/00* (2006.01)

(52) U.S. Cl.
USPC .............................. 600/26; 600/27

(58) Field of Classification Search
USPC ................. 600/26–28, 21, 22; 128/897, 898; 607/62
See application file for complete search history.

(56) References Cited

U.S. PATENT DOCUMENTS

| | | | |
|---|---|---|---|
| 3,388,699 A | 6/1968 | Webb et al. | |
| 3,464,416 A | 9/1969 | Williams | |
| 3,669,119 A | 6/1972 | Symmes | |
| 3,672,354 A | 6/1972 | Weber | |
| 3,762,396 A | 10/1973 | Ballentine et al. | |
| 4,418,687 A | 12/1983 | Matsumoto et al. | |
| 5,024,650 A | 6/1991 | Hagiwara et al. | |
| 5,064,410 A | 11/1991 | Frenkel et al. | |
| 5,167,610 A | 12/1992 | Kitado et al. | |
| 5,643,173 A | 7/1997 | Welles | |
| 6,108,580 A | 8/2000 | Greenspan et al. | |
| 6,468,234 B1 * | 10/2002 | Van der Loos et al. | 600/595 |
| 6,484,062 B1 | 11/2002 | Kim | |
| 6,520,905 B1 | 2/2003 | Surve et al. | |
| 6,554,763 B1 | 4/2003 | Amano et al. | |
| 6,836,681 B2 | 12/2004 | Stabler et al. | |
| 6,981,943 B2 | 1/2006 | Noguchi et al. | |
| 7,041,049 B1 | 5/2006 | Raniere | |
| 2002/0007124 A1 * | 1/2002 | Woodward | 600/481 |
| 2003/0023133 A1 | 1/2003 | Ashenden | |
| 2003/0171643 A1 | 9/2003 | Noguchi et al | |

(Continued)

FOREIGN PATENT DOCUMENTS

WO WO 2007105127 A1 * 9/2007

*Primary Examiner* — Charles A Marmor, II
*Assistant Examiner* — Shannon Canty
(74) *Attorney, Agent, or Firm* — Timothy A. Nathan

(57) ABSTRACT

A system configured to provide breathing cues to a patient to alleviate insomnia or sleeplessness. In one embodiment, the system comprises a pressure support apparatus, a patient monitor, and a processor. The pressure support apparatus is configured to provide a pressurized flow of gas for delivery to an airway of the patient. The patient monitor configured to generate one or more signals that convey information related to one or more physiological functions of the patient. The processor in operative communication with each of the pressure support apparatus and the patient monitor. The processor is configured (i) to determine whether the patient is asleep or awake based at least in part on the one or more signals generated by the patient monitor, and (ii) to control the pressure support apparatus such that if the patient is determined to be awake, one or more properties of the flow of gas are varied according to a first predetermined algorithm designed to provide breathing cues to the patient that prompt the patient to breathe at a target breathing rate.

14 Claims, 4 Drawing Sheets

(56) References Cited

U.S. PATENT DOCUMENTS

| | | |
|---|---|---|
| 2004/0224822 A1 | 11/2004 | Verheem |
| 2004/0225179 A1 | 11/2004 | Kaplan |
| 2004/0225340 A1 | 11/2004 | Evans |
| 2005/0187426 A1 | 8/2005 | Elliott |
| 2005/0209503 A1 | 9/2005 | Elliott |
| 2005/0209504 A1 | 9/2005 | Elliott |
| 2006/0041196 A1* | 2/2006 | Matthews et al. ............. 600/393 |
| 2006/0106275 A1 | 5/2006 | Raniere |
| 2006/0118112 A1* | 6/2006 | Cattano et al. ........... 128/204.21 |
| 2007/0083079 A1* | 4/2007 | Lee et al. ........................ 600/27 |
| 2007/0179334 A1* | 8/2007 | Groves et al. ................... 600/28 |
| 2008/0035147 A1 | 2/2008 | Kirby |

* cited by examiner

SYSTEM AND METHOD OF TREATMENT FOR INSOMNIA AND OCCASIONAL SLEEPLESSNESS

CROSS-REFERENCE TO RELATED APPLICATIONS

This application claims priority under 35 U.S.C. §119(e) from provisional U.S. patent application No. 60/915,490 filed May 2, 2007 the contents of which are incorporated herein by reference.

BACKGROUND OF THE INVENTION

1. Field of the Invention

The invention relates to the treatment of patients for insomnia and occasional sleeplessness.

2. Description of the Related Art

Insomnia and sleeplessness are known to affect a vast number of individuals. However, treatment of the symptoms of these conditions is generally accomplished with pharmacological agents. Since some people are averse to using drugs to treat seemingly benign conditions such as insomnia and sleeplessness, a need exists for an effective non-drug treatment.

SUMMARY OF THE INVENTION

One aspect of the invention relates to a system configured to provide breathing cues to a patient to alleviate insomnia or sleeplessness. In one embodiment, the system comprises a pressure support apparatus, a patient monitor, and a processor. The pressure support apparatus is configured to provide a pressurized flow of gas for delivery to an airway of the patient. The patient monitor is configured to generate one or more signals that convey information related to one or more physiological functions of the patient. The processor in operative communication with each of the pressure support apparatus and the patient monitor. The processor is configured (i) to determine whether the patient is asleep or awake based at least in part on the one or more signals generated by the patient monitor, and (ii) to control the pressure support apparatus such that if the patient is determined to be awake, one or more properties of the flow of gas are varied according to a first predetermined algorithm designed to provide breathing cues to the patient that prompt the patient to breathe at a target breathing rate.

Another aspect of the invention relates to a method of providing breathing cues to a patient to alleviate insomnia or sleeplessness. In one embodiment, the method comprises providing a pressurized flow of gas for delivery to an airway of the patient; generating one or more signals that convey information related to one or more physiological functions of the patient; determining whether the patient is asleep or awake based at least in part on the one or more generated signals; and, if the patient is determined to be awake, varying one or more properties of the flow of gas according to a first predetermined algorithm designed to provide breathing cues to the patient that prompt the patient to breathe at a target breathing rate.

Another aspect of the invention relates to a system configured to provide breathing cues to a patient to alleviate insomnia or sleeplessness. In one embodiment, the system comprises means for providing a pressurized flow of gas for delivery to an airway of the patient; means for generating one or more signals that convey information related to one or more physiological functions of the patient; means for determining whether the patient is asleep or awake based at least in part on the one or more generated signals; and means for varying one or more properties of the flow of gas according to a first predetermined algorithm designed to provide breathing cues to the patient that prompt the patient to breathe at a target breathing rate if the patient is determined to be awake.

Another aspect of the invention relates to a system configured to provide breathing cues to a patient to alleviate insomnia or sleeplessness, the system being configured to provide the breathing cues to the patient as the patient is supported by a support surface. In one embodiment, the system comprises a feedback system, a patient monitor, and a processor. The feedback system is configured to provide breathing cues to the patient via one or more feedback mechanisms. The patient monitor is configured to generate one or more signals that convey information related to one or more physiological functions of the patient. The patient monitor comprises one or more sensors configured to generate one or more signals that convey information related to the interaction of the patient with the support surface. The processor is in operative communication with each of the feedback system and the patient monitor. The processor is configured (i) to determine information related to at least one of the one or more physiological functions based at least in part on the one or more signals generated by the patient monitor, and (ii) to control the feedback system to provide the breathing cues to the patient according to a predetermined algorithm designed to prompt the patient to breathe at a target breathing rate.

Another aspect of the invention relates to a method of providing breathing cues to a patient to alleviate insomnia or sleeplessness, the breathing cues being provided to the patient as the patient is supported by a support surface. In one embodiment, the method comprises generating one or more signals that convey information related to interaction of the patient with the support surface; determining information related to at least one of one or more physiological functions of the patient based at least in part on the generated one or more signals; and providing breathing cues to the patient via one or more feedback mechanisms, the breathing cues being provided according to a predetermined algorithm designed to prompt the patient to breathe at a target breathing rate.

Another aspect of the invention relates to a system configured to provide breathing cues to a patient to alleviate insomnia or sleeplessness, the system being configured to provide the breathing cues to the patient as the patient is supported by a support surface. In one embodiment, the system comprises means for providing breathing cues to the patient via one or more feedback mechanisms; means for generating one or more signals that convey information related to interaction of the patient with the support surface; means for determining information related to at least one of one or more physiological functions of the patient based at least in part on the generated one or more signals; and means for providing breathing cues via one or more feedback mechanisms, the breathing cues being provided according to a predetermined algorithm designed to prompt the patient to breathe at a target breathing rate.

Another aspect of the invention relates to a system configured to provide breathing cues to a patient to alleviate insomnia or sleeplessness. In one embodiment, the system comprises a feedback system, an environment monitor, and a processor. The feedback system is configured to provide breathing cues to the patient via a plurality of feedback mechanisms. The environment monitor is configured to generate one or more signals that convey information related to one or more ambient conditions of an environment that surrounds the patient. The processor is in operative communication with each of the feedback system and the environment monitor. The processor is configured (i) to determine at least one of the one or more ambient conditions based on the one or more signals generated by the environment monitor, and (ii) to control the feedback system to provide breathing cues to the patient according to a predetermined algorithm designed to prompt the patient to breathe at a target breathing rate, wherein the processor controls the feedback system such that one or more of the plurality of feedback mechanisms are implemented to provide the breathing cues to the patient based on the determined at least one of the one or more ambient conditions.

Another aspect of the invention relates to a method of providing breathing cues to a patient to alleviate insomnia or sleeplessness. In one embodiment, the method comprises generating one or more signals that convey information related to one or more ambient conditions of an environment that surrounds the patient; determining at least one of the one or more ambient conditions based on the generated one or more signals; and providing breathing cues to the patient via a plurality of feedback mechanisms according to a predetermined algorithm designed to prompt the patient to breathe at a target breathing rate, wherein the one or more of the plurality of feedback mechanisms are implemented to provide the breathing cues to the patient based on the determined at least one of the one or more ambient conditions.

Another aspect of the invention relates to a system configured to provide breathing cues to a patient to alleviate insomnia or sleeplessness. In one embodiment, the system comprises means for generating one or more signals that convey information related to one or more ambient conditions of an environment that surrounds the patient; means for determining at least one of the one or more ambient conditions based on the generated one or more signals; and means for providing breathing cues to the patient via a plurality of feedback mechanisms according to a predetermined algorithm designed to prompt the patient to breathe at a target breathing rate, wherein the one or more of the plurality of feedback mechanisms are implemented to provide the breathing cues to the patient based on the determined at least one of the one or more ambient conditions.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE EXEMPLARY EMBODIMENTS

Figure 1:
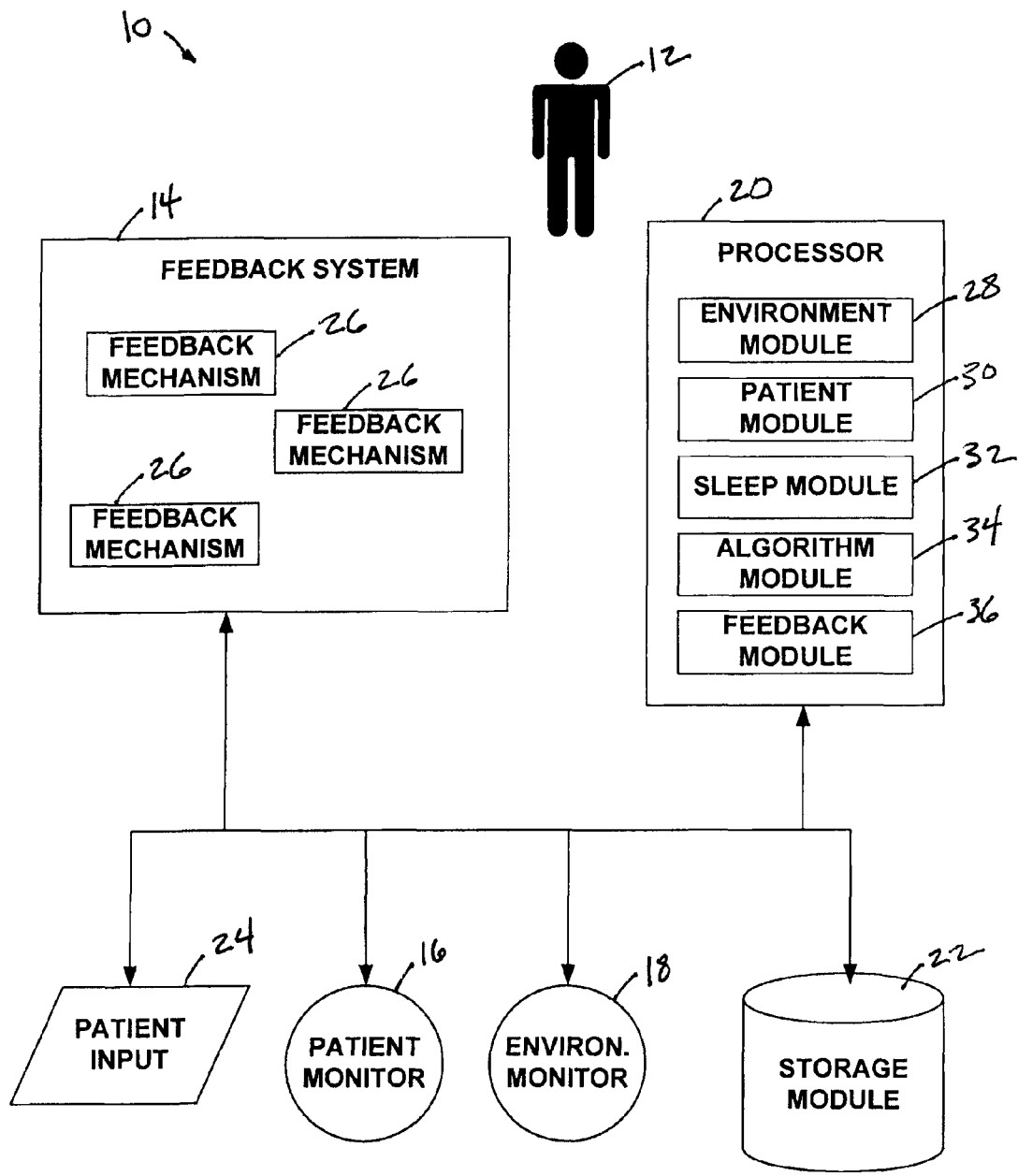
FIG. 1 illustrates a system configured to provide breathing cues to a patient to alleviate insomnia and/or sleeplessness, in accordance with one embodiment of the invention.

FIG. 1 is a schematic diagram of a system 10 configured to provide breathing cues to a patient 12 to alleviate insomnia and/or sleeplessness. The breathing cues are provided to the patient 12 according to a predetermined algorithm that is designed to prompt the patient 12 to breathe at a target breathing rate. The target breathing rate may be a finite rate, or it may include an acceptable range of rates. The target breathing rate is a therapeutically significant breathing rate that typically enables patients to relax into sleep. In one embodiment, system 10 includes a feedback system 14, a patient monitor 16, an environment monitor 18, a processor 20, a storage module 22, and a patient input 24. It should be appreciated that although system 10 is discussed herein as a treatment to alleviate insomnia and/or sleeplessness, this is not intended to be limiting. One of ordinary skill in the art should appreciate that the implementation of system 10 to prompt the patient 12 to breathe at a target breath rate may be used to treat a myriad of conditions and/or ailments. For example, controlled breathing accomplished by implementing system 10 may be used to treat hypertension, obesity, migraine, anxiety, restless legs syndrome, chronic fatigue/fibromyalgia, mood disorders, and/or other conditions or ailments.

Feedback system 14 is configured to provide breathing cues to the patient 12 via one or more feedback mechanisms 26. As used herein, "breathing cues" refers to any sensory signals that are provided to the patient to communicate information about how the patient should breathe. For example, these cues may communicate general information about the current breathing rate at which the user is breathing (e.g., "faster," "slower," etc.). As another example, these cues may communicate information related to the timing of transition points in the breathing of the patient (e.g., "begin inhale," "begin exhale," etc.).

The one or more feedback mechanisms 26 may include any number of different sensory communication mechanisms. For instance, in one embodiment, feedback mechanisms 26 may include an auditory device (e.g., a speaker), a visual indicator (e.g., a light or series of lights, an electronic visual display, a movable member such as a needle, etc.), a tactile indicator that delivers tactile feedback to the patient 12 (e.g., a vibrating member that vibrates, for example, at different rates/intensities), a respiratory indicator (e.g., a pressure support apparatus that delivers a pressurized flow of gas to an airway of patient 12), an olfactory indicator capable of providing different smells to the patient 12, a thermal indicator capable of changing temperatures to communicate information to the patient 12, and/or a taste indicator capable of providing gustatory stimulation to the patient 12, and/or any combination of the above. In one embodiment, feedback mechanisms 26 include a vestibular stimulation indicator that provides galvanic stimulation to the vestibular region of patient 12's brain. This may be experienced by patient 12 as a rocking motion that varies in rate and/or intensity to communicate breathing cues. An exemplary vestibular stimulation indicator is described, for example, in U.S. Pat. No. 6,748,275, issued Jun. 8, 2004, and entitled, "Vestibular Stimulation System and Method," hereby incorporated by reference in its entirety.

Patient monitor 16 is configured to generate one or more signals that convey information related to one or more physiological functions of patient 12. The one or more physiological functions may include, for example, a respiration rate, a pulse rate, a pulse rate variability, gross motor activity, a body temperature, and/or other physiological functions. As such, patient monitor 16 includes one or more sensors that monitor patient 12. In one embodiment, the sensors of patient monitor 16 monitor the one or more physiological functions of patient 12 without being "mounted" to patient 12. In some instances, the sensors of patient monitor 16 may not even contact patient 12 directly. Although other embodiments, in which one or more of the sensors include portions that are directly mounted to patient 12, are contemplated, embodiments that do not include sensors that are directly mounted to patient 12 may increase the comfort and/or ease of use of system 10 by patient 12. Some exemplary descriptions of sensors that may be included in patient monitor 16 are presented below.

Environment monitor 18 is configured to generate one or more signals that convey information related to one or more ambient conditions of an environment that surrounds patient 12. The one or more ambient conditions may include, for example, an ambient light level, one or more frequency ranges of ambient light, an ambient noise level, one or more frequency ranges of ambient noise, a temperature, a humidity, and/or other ambient conditions. To this end, environment monitor 18 includes one or more sensors, as known in the art, that monitor ambient conditions.

Storage module 22 provides electronic storage capabilities for system 10. Storage module 22 includes one or more electronically readable storage media that are operatively coupled with processor 20. This operative couple is illustrated with an arrow in FIG. 1. The electronically readable storage media of storage module 22 may include one or both of system storage that is provided integrally (i.e., substantially non-removable) with system 10 and removable storage that is removably connectable to system 10 via, for example, a port (e.g., a USB port, a firewire port, etc.) or a drive (e.g., a disk drive, etc.). Storage module 22 may include optically readable storage media (e.g., optical disks, etc.), magnetically readable storage media (e.g., magnetic tape, magnetic hard drive, floppy drive, etc.), solid-state storage media (e.g., flash drive, etc.), and/or other electronically readable storage media. In one embodiment, storage module 22 may include a smart card with writeable memory that receives information from and provides information to system 10 wirelessly. Storage module 22 may store software algorithms, data, and/or other information that enable processor 20 to function properly.

Patient input 24 provides an interface between processor 20 and patient 12 and/or some other user (e.g., a caregiver, etc.) through which patient 12 (and/or some other user) may provide information to system 10. This enables information, data and/or instructions and any other communicable items, collectively referred to as "information", to be communicated between patient 12 and processor 20. This information may be communicated from patient input 24 to processor 20 by an operative communication link illustrated in FIG. 1 by an arrow. Examples of conventional input devices suitable for inclusion in patient input 24 include a keypad, buttons, switches, or keyboard.

It is to be understood that other communication techniques, either hard-wired or wireless, are also contemplated by the present invention as patient input 24. For example, the present invention contemplates that patient input 24 may be integrated with a removable storage interface provided by storage module 22. In this example, information may be loaded into processor 20 from removable storage (e.g., a smart card, a flash drive, a removable disk, etc.) that enables patient 12 to customize the implementation of system 10. Other exemplary input devices and techniques adapted for use with the pressure support system 10 as patient input 24 include, but are not limited to, an RS-232 port, RF link, an IR link, modem (telephone, cable or other). In short, any technique for providing information to processor 20 is contemplated by the present invention as patient input 24.

Processor 20 is configured to provide information processing capabilities in system 10. As such, processor 20 may include one or more of a digital processor, an analog processor, a digital circuit designed to process information, an analog circuit designed to process information, a state machine, and/or other mechanisms for electronically processing information. Although processor 20 is shown in FIG. 1 as a single entity, this is for illustrative purposes only. In some implementations, processor 20 may include a plurality of processing units. These processing units may be physically located within the same device, or processor 20 may represent processing functionality of a plurality of devices operating in coordination. In instances in which a plurality of devices are implemented, operative communications links may be formed between the devices to enable communication and coordination therebetween. For example, in some embodiments, processor 20 may include one or more processors external to the other components of system 10 (e.g., a host computer), one or more processors that are included integrally in one or more of the components of system 10 (e.g., one or more processors included integrally with one or more of feedback mechanisms 26, with patient monitor 16, with environmental monitor 18, with storage module 22, etc.), or both. Processors external to other components within system 10 may, in some cases, provide redundant processing to the processors that are integrated with components in system 10, and/or the external processor(s) may provide additional processing to determine additional information related to the operation of system 10 and/or the provision of breathing cues to patient 12.

As is shown in FIG. 1, in one embodiment, processor 20 includes an environment module 28, a patient module 30, a sleep module 32, an algorithm module 34, and a feedback module 36. Modules 28, 30, 32, 34, and/or 36 may be implemented in software; hardware; firmware; some combination of software, hardware, and/or firmware; and/or otherwise implemented. It should be appreciated that although modules 28, 30, 32, 34, and/or 36 are illustrated in FIG. 1 as being co-located within a single processing unit, in implementations in which processor 20 includes multiple processing units modules 28, 30, 32, 34, and/or 36 may be located remotely from the other modules and operative communication between modules 28, 30, 32, 34, and/or 36 may be achieved via one or more communication links. Such communication links may be wireless or hard wired.

Environment module 28 receives the one or more signals generated by environment monitor 18 and, based on the one or more signals, determines information related to one or more of the ambient conditions of the environment that surrounds patient 12. For example, as mentioned above with respect to environment monitor 18, the one or more ambient conditions may include an ambient light level, one or more frequency ranges of ambient light, an ambient noise level, one or more frequency ranges of ambient noise, a temperature, a humidity, and/or other ambient conditions. One or more appropriate sensors known in the art can be used by the environment monitor 18 to detect the environmental condition and to generate the corresponding signal based on the environmental condition. As is discussed further below, the determined one or more ambient conditions may be implemented in the control of system 10 by processor 20.

Patient module 30 receives the one or more signals generated by patient monitor 16 and, based on the one or more signals, determines information related to one or more physiological functions of patient 12. For instance, as was discussed above with respect to patient monitor 16, the one or more physiological functions may include a respiration rate, a pulse rate, a pulse rate variability, gross motor activity, a body temperature, electroencephalogram ("EEG"), electrooculogram ("EOG"), and/or other physiological functions. As is described further below, one or more of the determined physiological functions related to the breathing of patient 12 (e.g., breathing rate, etc.) can be used in one embodiment to prompt patient 12 to breathe at the target breathing rate. In one embodiment, information related to the physiological function(s) determined by patient module 30 is implemented to determine the sleep state of patient 12 (e.g., asleep, awake, etc.).

Sleep module 32 is configured to determine the sleep state of patient 12. In one embodiment, sleep module 32 determines the sleep state of patient 12 based on information related to one or more physiological functions that is determined by patient module 30. For example, sleep module 32 may employ known patterns in respiration rate, pulse rate, pulse rate variability, gross motor activity, body temperature, EEG, EOG, and/or other physiological functions that relate to changes in the sleep state of patient 12 to determine the sleep state of patient 12. In some instances, the determination of the sleep state includes a determination of whether patient 12 is asleep or awake. However, the determination of sleep state by sleep module 32 based on physiological functions of patient 12 is not necessarily restricted to this. For example, in one embodiment, sleep module 32 determines a state of sleep that patient 12 is experiencing during a typical sleep cycle (e.g., Rapid Eye Movement, etc.).

Algorithm module 34 is configured to determine an appropriate algorithm (if any) that should be used to control feedback system 14, and to implement the appropriate algorithm to determine how feedback system 14 should be controlled. One of the predetermined algorithms implemented by algorithm module 34 is designed to control feedback system 14 to provide breathing cues to patient 12 that prompt patient 12 to breathe at a target breathing rate. This predetermined algorithm employed by algorithm module 34 dictates (1) which of feedback mechanisms 26 is implemented to provide the breathing cues to patient 12, and (2) the breathing cues that are provided patient 12 (e.g., the timing of the breathing cues, the content of the breathing cues, etc.).

In one embodiment, the predetermined algorithm determines which of feedback mechanisms 26 to implement in providing the breathing cues to patient 12 based on one or more factors. The one or more factors may include, for example, a user preference, a system default, an ambient condition, a physiological function of patient 12, and/or other factors. Based on the one or more factors the predetermined algorithm may be configured to discontinue the implementation of one or more of feedback mechanisms 26, begin the implementation of one or more of feedback mechanisms 26, and/or switch the implementation of one feedback mechanism 26 with another one of feedback mechanisms 26.

An example of controlling feedback system 14 based on an ambient condition (or conditions) would include monitoring the ambient condition(s) to determine if it has fallen below, or risen above, a condition threshold. As an example of a user preference, patient 12 may communicate with system 10 (e.g., via patient input 24) to set a combination of preferred feedback mechanisms 26 by which patient 12 would prefer to receive breathing cues. An example of a system default may include a combination of preferred feedback mechanisms 26 by which system 10 provides breathing cues to patient 12 that have been preconfigured in system 10. It should be appreciated that in some instances, user preferences may be communicated by patient 12 to system 10 to replace a previously preconfigured system default.

As was mentioned above, in one embodiment the predetermined algorithm dictates which feedback mechanisms 26 should be implemented by system 10 based on one or more ambient conditions (e.g., determined by environment module 28). As an example, the predetermined algorithm may dictate that if the ambient light level of the environment surrounding patient 12 is below a light level threshold, then system 10 implements a visual feedback mechanism 26 that includes an indicator light to provide the breathing cues to patient 12. However, if the ambient light level of the environment rises above the light level threshold, which is set at an ambient light level above which emissions of the visual feedback mechanism 26 becomes difficult to see, the predetermined algorithm dictates the cessation of providing the breathing cues to patient 12 using the visual feedback mechanism 26. The ambient light level may be determined using substantially the entire spectrum of visible light. Or, the ambient light level may be determined for one or more specific frequency ranges (e.g., a frequency range of radiation emitted by feedback mechanism 26). In some instances, the cessation of providing the breathing cues to patient 12 using the visual feedback mechanism 26 may be accompanied by the implementation of another feedback mechanism 26 (e.g., an auditory feedback mechanism 26). As another example, if the ambient noise level of the environment is below a noise level threshold, the predetermined algorithm dictates that an auditory feedback mechanism 26 be implemented to provide breathing cues to patient. If the ambient noise level rises above the noise level threshold, then the predetermined algorithm dictates that the auditory feedback mechanism 26 no longer be implemented and/or that another feedback mechanism 26 be implemented (e.g., a visual feedback mechanism 26, a tactile feedback mechanism, etc.). In some instances, the response of the predetermined algorithm to ambient conditions in controlling feedback mechanisms 26 is determined, at least in part, based on user preferences and/or system defaults. In some cases, user preferences may include "real time" control input by patient 12 to system 10 that specifies the current levels of feedback, and or the preferred feedback mechanism(s) 26.

In one embodiment, the predetermined algorithm dictates which of feedback mechanisms 26 is implemented to provide breathing cues to patient 12 based on one or more physiological functions (e.g., as determined by patient module 30). For example, if the eyes of patient 12 are closed, then the predetermined algorithm may dictate that the implementation of a visual feedback mechanism 26 be halted and/or substituted. As another example, the body position of patient 12 may be determined, and breathing cues may be provided to patient 12 based on the determined body position. For instance, visual breathing cues may be provided to patient 12 within what is determined to be patient 12's field of vision, based on the determined body position. As yet another example, a body temperature of patient 12 may be determined, and the breathing cues may be adjusted based on this body temperature. For instance, if the body temperature of patient 12 indicates that patient 12 is relatively cold, the temperature of a flow of gas being implemented to provide the breathing cues may be increased. Similarly, if the body temperature of patient 12 indicates that patient 12 is relatively warm, the temperature of the flow of gas may be decreased. In some instances, the response of the predetermined algorithm to physiological functions in controlling feedback mechanisms 26 is determined, at least in part, based on user preferences and/or system defaults.

It should be appreciated that in some embodiments the predetermined algorithm varies the implementation of feedback system 14 to provide the breathing cues based on both of ambient conditions and physiological functions. In other embodiments, the predetermined algorithm only varies the implementation of feedback system 14 to provide the breathing cues based on one or the other of ambient conditions and physiological functions. In still other embodiments, the predetermined algorithm does not vary the implementation of feedback system 14 based on either of ambient conditions and physiological functions.

As was mentioned above, in one embodiment, the predetermined algorithm dictates the timing and/or content of the breathing cues in order to prompt patient 12 to breathe at the target breathing rate. This will include prompting patient 12 to transition from inhaling to exhaling, and vice versa, such that the breathing of patient 12 is accomplished at the target breathing rate. In some instances, the breathing cues are simply provided at the target breathing rate. In other instances, the predetermined algorithm takes into account an actual breathing rate of patient 12 (e.g., as determined by patient module 30), and coaxes patient 12 in an incremental manner to reduce a difference between the actual breathing rate and the target breathing rate. For example, the predetermined algorithm may deliver the breathing cues to patient 12 according to the timing described in U.S. Patent Application Publication No. 2008-0035147, filed Aug. 11, 2006, and entitled "Systems and Methods for Controlling Breathing Rate" ("the '205 application"), hereby incorporated by reference in its entirety.

In one embodiment, the selection of a predetermined algorithm by algorithm module 34 to control feedback system 14 is based on a determination of whether patient 12 is asleep or awake. For example, if sleep module 32 determines that patient 12 is awake, then algorithm module 34 will implement a predetermined algorithm to control feedback system 12 in order to provide breathing cues to patient 12 that prompt patient 12 to breathe at the target breathing rate (e.g., as described above). On the other hand, in one embodiment, if sleep module 32 determines that patient 12 is asleep, then algorithm module 34 will stop providing breathing cues to patient 12 that prompt patient 12 to breathe at the target breathing rate. Instead, algorithm module 34 may determine that a different algorithm should be used to control feedback system 14. For instance, as is discussed further below, when patient 12 is determined to be asleep, algorithm module 34 may determine that an algorithm should be implemented to control feedback system 14 that provides a therapeutic value to a sleeping patient 12 (e.g., a pressure support algorithm). As another example, algorithm module 34 may determine that one or more of feedback mechanisms 26 should simply be left inactive while patient 12 sleeps.

In one embodiment, if sleep module 32 determines that patient 12 has awakened from being asleep, algorithm module 34 automatically re-initiates control of the feedback system 14 to again provide breathing cues to patient 12 according to the predetermined algorithm designed to prompt patient 12 to breathe at the target breathing rate. In some instances, the re-initiation may only take place if patient 12 is determined to have woken up and remains awake for a predetermined period of time. In another embodiment, once patient 12 has fallen asleep, algorithm module 34 only re-initiates the provision of breathing cues according to the predetermined algorithm if some predetermined signal is given to system 10 by patient 12 (e.g., an input is provided to system via patient input 24). In some implementations, the predetermined signal leads to the re-initiation of the provision of breathing cues only if sleep module 32 indicates that patient 12 is awake. This may prevent patient 12 from inadvertently triggering the re-initiation of the breathing cues while still asleep.

Feedback module 36 controls feedback system 14 according to the predetermined algorithm that is implemented by algorithm module 34. This may include activating and deactivating various ones of feedback mechanisms 26 in accordance with the predetermined algorithm and/or controlling the outputs of feedback mechanisms 26 according to the outputs determined for feedback mechanisms 26 by algorithm module 34 by implementing the predetermined algorithm.

In one embodiment, the effectiveness of system 10 in aiding patient 12 to fall asleep is monitored by processor 20. This may include, for example, determining an amount of time that patient 12 receives treatment from system 10 prior to falling asleep. As other examples, the amount of time that patient 12 breathes at the target breathing rate and/or the amount of time that it takes for the breathing cues provided by system 10 to bring the breathing rate of patient 12 to the target breathing rate may provide metrics of the effectiveness of system 10. In one embodiment, this information is saved to storage module 22. This information may be saved in conjunction with other information related to the operation of system 10. For example, the particular implementation of feedback system 14 to deliver breathing cues to patient 12 (e.g., which of feedback mechanisms 26 is implemented) may also be saved to storage module 22.

Saving information about the effectiveness and/or operation of system 10 to storage module 22 enables this information to be accessed by system 10, patient 12, and/or a caregiver (e.g., a doctor, a nurse, etc.) at a later time. For instance, system 10 may implement the information to adjust system defaults (e.g., regarding the implementation of feedback system 14) based on which feedback mechanisms 26 are most effective in aiding patient 12 in breathing at the target breathing rate and/or falling asleep. As another example, a caregiver may access the information in order to monitor overall trends in the breathing and/or sleeping patterns (and/or correlations therebetween) of patient 12. In one embodiment, storage module 22 is adapted to communicate with a removable electronic storage medium (e.g., a flash drive, a smart card, etc.) that is associated with one or more patients. This enables system 10 to adapt system defaults to enhance its effectiveness in providing treatment to a particular patient based on the information stored on the removable electronic storage medium that is associated with the patient. In one embodiment, patient 12 provides an identifier to system 10 (e.g., via patient input 24) that identifies patient 12, and information related to the treatment of the identified patient is stored in storage module 22 separately from information related to the treatment of other patients.

Figure 2:
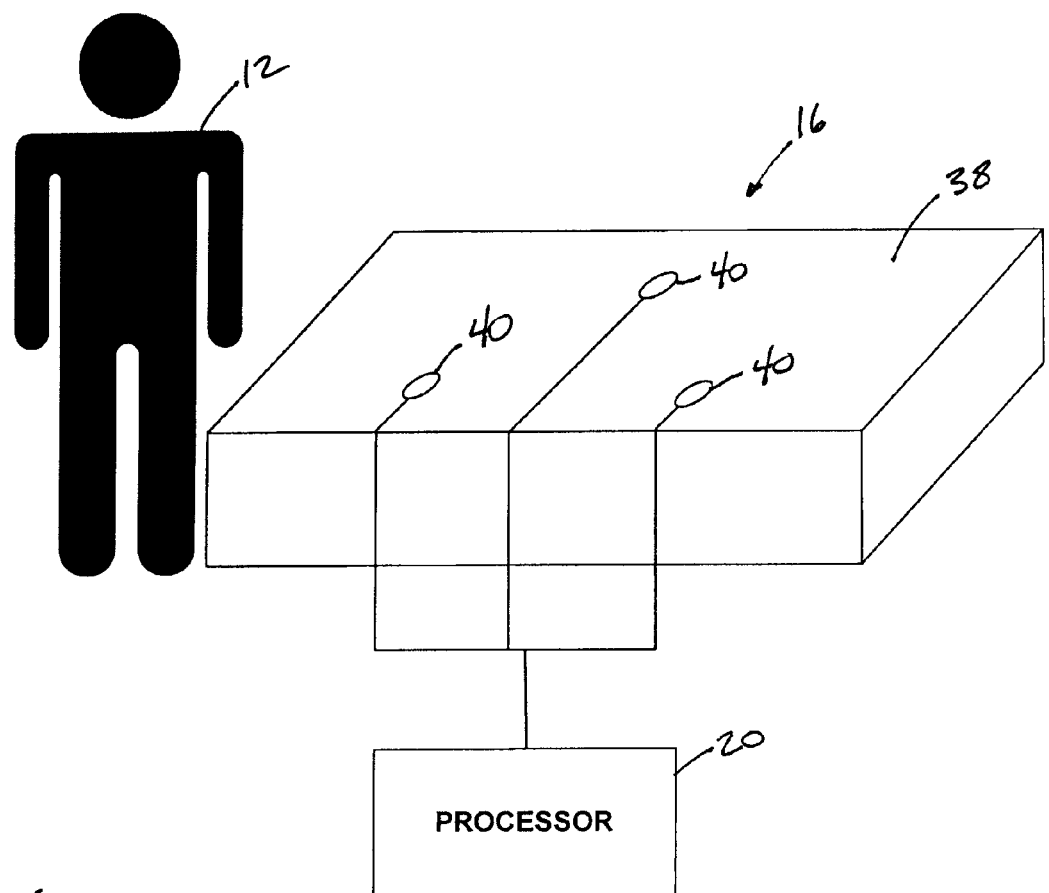
FIG. 2 illustrates a patient monitor, according to one embodiment of the invention.

FIG. 2 illustrates an implementation of patient monitor 16, in accordance with one or more embodiments of the invention. In the embodiment shown in FIG. 2, patient monitor 16 is adapted to monitor patient 12 as patient 12 is supported on a support surface 38. Support surface 38 is a surface adapted to provide a comfortable substrate upon which patient 12 may rest or sleep. For example, support surface 38 may be provided by a bed mattress, a gurney, a cot, a lounge, a hammock, a sofa, a comfortable chair, etc. As can be seen in FIG. 2, in order to monitor one or more physiological functions of patient 12, patient monitor 16 includes one or more sensors 40 configured to generate one or more signals that convey information related to the interaction of patient 12 with support surface 38.

Sensors 40 are disposed at or near support surface 38. For example, in one embodiment, sensors 40 are included within a mattress or cushion that provides support surface 38. In one embodiment, sensors 40 are placed by a user (e.g., patient 12, a caregiver, etc.) on support surface 38. In such an embodiment, sensors 40 may be covered by a sheet or cover that envelopes the mattress providing support surface 38, which secures sensors 40 in place on support surface 38 between patient 12 and support surface 38. In one embodiment, sensors 40 are disposed integrally into a cover (e.g., a blanket, a mat, a sheet, a mattress pad, a cover, a pillowcase, etc.) that is disposed on a mattress or cushion that provides at least a portion of support surface 38. It should be appreciated that a mattress or cushion providing at least a portion of support surface 38 may refer to a single body that provides substantially all of support surface 38 or to a body that cooperates with other similar structures to provide support surface 38 (e.g., one cushion of a sofa that includes a plurality of cushions). Further, the mattress or cushion may refer to a support structure used by patient 12 to support a single portion of her body while she rests and/or sleeps (e.g., a pillow to support the head of patient 12). In one embodiment, the mat, sheet, or cover itself is a sensor that has the ability to transduce a physical (or physiological) phenomenon into a signal that is usable by processor 20. In one embodiment, sensors 40 are placed in a covering (e.g., a blanket, a sheet, etc.) that is placed over patient 12.

As was mentioned above, sensors 40 are configured to generate one or more signals that convey information related to the interaction of patient 12 with support surface 38. In particular, the information conveyed by the one or more signals generated by sensors 40 enables the determination of information related to one or more physiological functions of patient 12. For example, sensors 40 may include one or more pressure sensors that generate one or more signals that convey information related to pressure applied by patient 12 to support surface 38. Based on signals generated by the one or more pressure sensors, information related to the respiration of patient 12 (e.g., breathing rate, breathing rate variability, etc.), information related to the vascular function of patient 12 (e.g., pulse rate, pulse rate variability, blood pressure, etc.), information related to gross motor activity of patient 12, and/or information related to other physiological functions of patient 12 may be determined. As another example, sensors 40 may include one or more accelerometers (or other motion detectors) that generate one or more signals that convey information related to motion of support surface 38 caused by physical interaction between support surface 38 and patient 12. Based on signals generated by the one or more accelerometers, information related to the respiration of patient 12 (e.g., breathing rate, breathing rate variability, etc.), information related to the vascular function of patient 12 (e.g., pulse rate, pulse rate variability, blood pressure, etc.), information related to gross motor activity of patient 12, and/or information related to other physiological functions of patient 12 may be determined. As another example, sensors 40 may include one or more thermal sensors that generate one or more signals that convey information related to heat exchanged between support surface 38 and patient 12. Based on the signals generated by the one or more thermal sensors, information related to a body temperature of patient 12 may be determined.

It should be appreciated that the types of sensors described above is not intended to be limiting. Other types of sensors that generate one or more signals that convey information related to other aspects of the interaction of patient 12 and support surface 38 are contemplated. For example, respiratory air flow from patient 12 may be received by a sensor in communication with an airway of patient 12. As another example, sensors 40 may include one or more sensors that emit energy (e.g., microwave, IR, UV, and/or visible electromagnetic radiation, sound waves, etc.) toward patient 12 and determine information related to patient 12 based on energy reflected from patient 12. Further, sensors 40 may include only one type of sensor, or sensors 40 may include a combination of the above-described types of sensors and/or other types of sensors.

Figure 3:
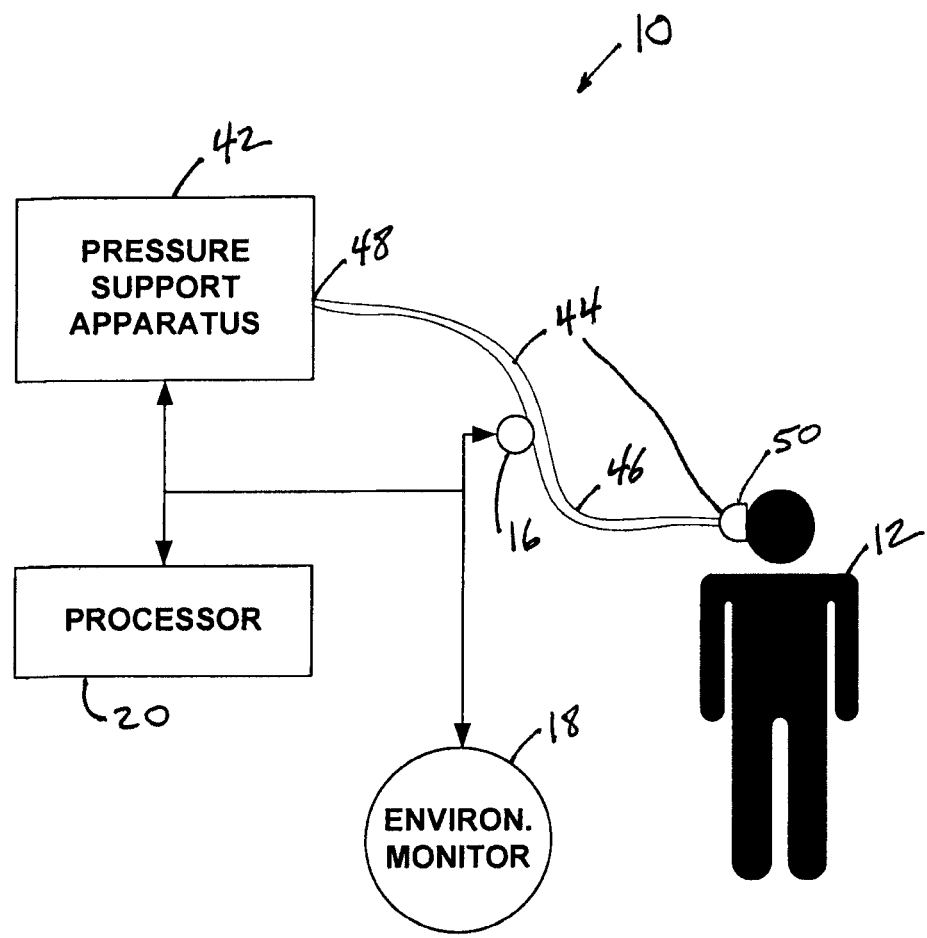
FIG. 3 illustrates a system configured to provide breathing cues to a patient to alleviate insomnia and/or sleeplessness, in accordance with one embodiment of the invention.

FIG. 3 illustrates system 10, in accordance with one or more embodiments of the invention. In the embodiment illustrated in FIG. 3, system 10 includes a pressure support apparatus 42. Pressure support apparatus 42 is configured to provide a pressurized flow of gas for delivery to an airway of patient 12. In providing the flow of gas to patient 12, pressure support apparatus 42 is capable of varying one or more properties of the gas (e.g., the composition, the pressure, the flow rate, the volume, etc.) to provide a therapeutic benefit to patient 12. For instance, the pressure of the flow of gas may be set and/or adjusted to minimize the occurrence and/or impact of one or more types of sleep-related respiratory events (e.g., apneas, hypopneas, flow limitations, Cheyne-Stokes respiration, etc.). One example of a pressure support apparatus is found in U.S. Patent Application Publication No. 2006-0118112, filed Jan. 27, 2006, and entitled "Sleep Apnea Treatment Device" ("the '002 application"), hereby incorporated by reference in its entirety.

The pressurized flow of gas is delivered from pressure support apparatus 42 to patient 12 via an external patient circuit 44. External patient circuit 44 includes a conduit 46 that is attached to an external coupling 48 of pressure support apparatus 42. A patient interface device 50 at the end of conduit 46 communicates the flow of gas in patient circuit 44 with the airway of patient 12. The present invention contemplates that patient interface device 50 is any device suitable for communicating an end of patient circuit 44 with the airway of patient 12. Examples of suitable patient interface devices include a nasal mask, oral mask or mouthpiece, nasal/oral mask, nasal cannula, trachea tube, intubation tube, hood or full face mask. It is to be understood that this list of suitable interface devices is not intended to be exclusive or exhaustive.

In the embodiment of system 10 shown in FIG. 3, pressure support apparatus 42 functions as a feedback mechanism (e.g., similar to feedback mechanisms 26 of feedback system 14, shown in FIG. 1 and described above). FIG. 3 illustrates pressure support apparatus 42 as being in operative communication with patient monitor 16, environment monitor 18, and processor 20. Although these components of system 10 are described below as being distinct from pressure support apparatus 42, it should be appreciated (e.g., from the disclosure incorporated herein by reference) that some or all of the functionality of patient monitor 16, environment monitor 18, and/or processor 20 may be provided by the integral components of pressure support apparatus 42 itself. Further, the functionality of other components of system 10 may be provided by pressure support apparatus 42 (e.g., storage module 22).

As shown in FIG. 3, patient monitor 16 includes one or more sensors which monitor one or more properties of the flow of gas. By monitoring the flow rate and/or pressure of the flow of gas, information related to the respiration of patient 12 may be determined. For example, the breathing rate, a current breathing cycle (e.g., currently inhaling, currently exhaling, etc.), transitions in the breathing cycle, and/or other information related to the respiration of patient 12 may be determined.

In one embodiment, processor 20 controls pressure support apparatus 42 such that the pressure of the flow of gas provided from pressure support apparatus 42 to patient 12 is varied according to a first predetermined algorithm to provide breathing cues to patient 12 to breathe at the target breathing rate. For example, the pressure may be elevated to prompt patient 12 to inhale (or to continue to inhale) and the pressure may be reduced to prompt patient 12 to exhale (or to continue to exhale). In one embodiment, the first predetermined algorithm takes into account information determined by processor 20 related to the respiration of patient 12 (e.g., based on the output of patient monitor 16). For example, the first predetermined algorithm may take into account an actual breathing rate of patient 12 and/or the specific timing of transitions in the breathing cycle of patient 12 (or as described in detail in the '205 application, incorporated by reference above).

As has been discussed above, in one embodiment, if processor 20 (e.g., sleep module 32 shown in FIG. 1 and described above) determines that patient 12 is awake based on one or more physiological functions monitored by patient monitor 16, then processor 20 (e.g., algorithm module 34 shown in FIG. 1 and described above) implements the first predetermined algorithm to determine the manner in which pressure support apparatus 42 should be controlled to provide the breathing cues to patient 12. If processor 20 determines that patient 12 is asleep by this analysis, then processor 20 ceases the implementation of the first predetermined algorithm to determine the manner in which pressure support apparatus 42 should be controlled. Further, in one embodiment, once it is determined that patient 12 is asleep, processor 20 implements a second predetermined algorithm to determine the manner in which pressure support apparatus 42 should be controlled. For example, the second predetermined algorithm may dictate that pressure support apparatus 42 be controlled such that the pressure of the flow of gas is set and/or adjusted to minimize the occurrence and/or impact of one or more types of sleep-related respiratory events. This may enhance the comfort of patient 12, since the flow of gas provided by pressure support apparatus 42 as pressure support apparatus 42 is operated according to the second predetermined algorithm may be considered uncomfortable by patient 12 when patient 12 is awake.

Figure 4:
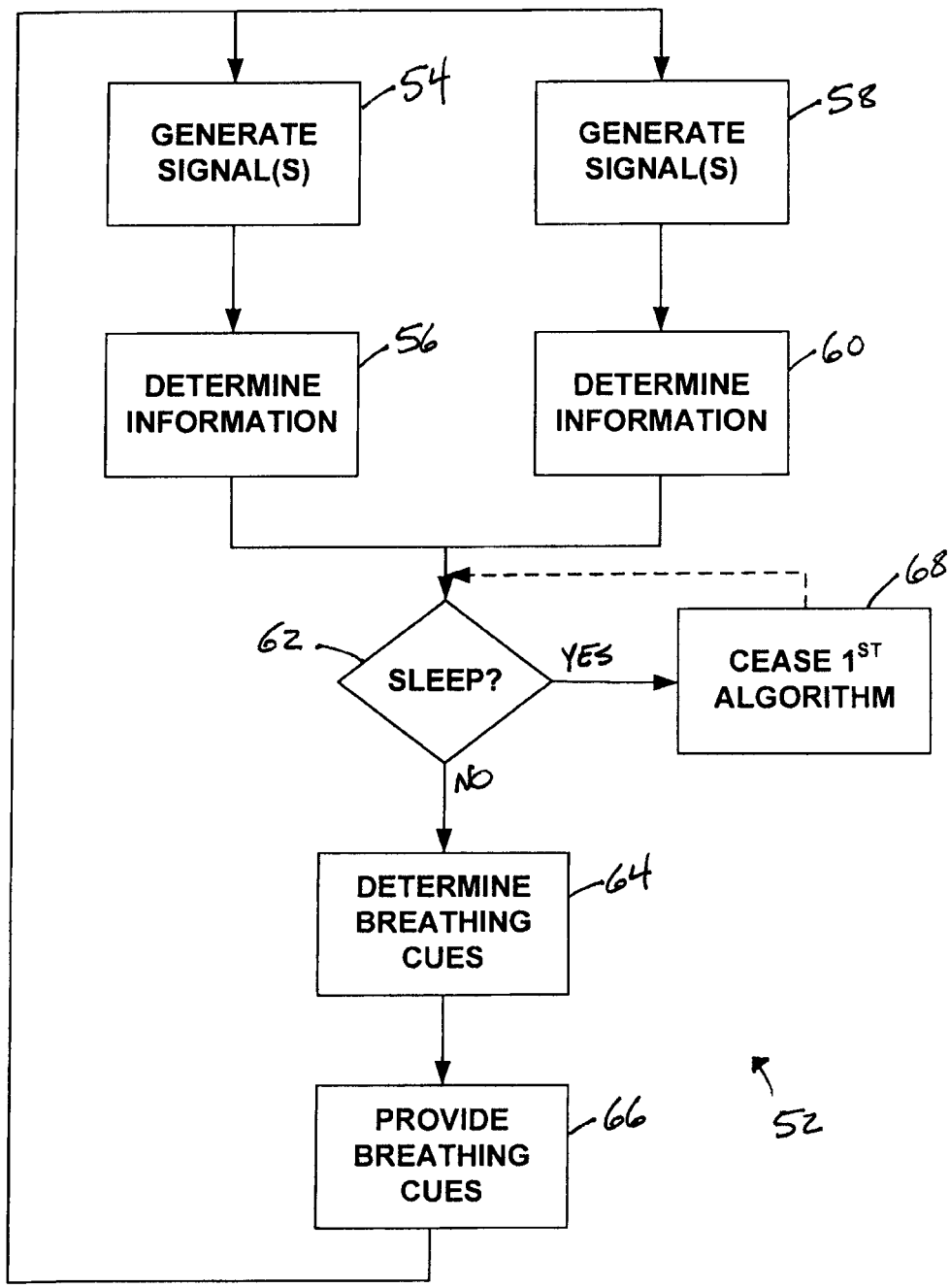
FIG. 4 illustrates a method of providing breathing cues to a patient to alleviate insomnia and/or sleeplessness, in accordance with one embodiment of the invention.

FIG. 4 illustrates a method 52 of providing breathing cues to a patient to alleviate insomnia or sleeplessness, in accordance with one embodiment of the invention. It should be appreciated that although specific reference is made below regarding various operations of method 52 that can be executed by components of system 10 (e.g., illustrated in FIGS. 1-3 and described above), this is for illustrative purposes only. In other embodiments, systems other than system 10 may be implemented to execute some or all of the operations of method 52.

Method 52 includes an operation 54 at which one or more signals that convey information related to one or more physiological functions of the patient are generated. In one embodiment, operation 54 is performed by a patient monitor similar to patient monitor 16 shown in FIGS. 1-3 and described above. As such, the one or more signals may convey information related to an interaction of the patient with a support surface, information related to one or more properties of a flow of gas being delivered to the patient, and/or other information.

At an operation 56, information related to one or more physiological functions of the patient is determined. The information determined at operation 56 is determined based on the signals generated at operation 54. In one embodiment, operation 56 is performed by a processor similar to processor 20 shown in FIGS. 1-3 and described above, and, more particularly, by a patient module provided by the processor similar to patient module 30 shown in FIG. 1 and described above.

At an operation 58, one or more signals that convey information related to one or more ambient conditions in an environment surrounding the patient are generated. In one embodiment, operation 58 is performed by an environment monitor similar to environment monitor 18 shown in FIGS. 1 and 3 and described above.

At an operation 60, information related to one or more ambient conditions of the environment surrounding the patient is determined. The information determined at operation 60 is determined based on the signals generated at operation 58. In one embodiment, operation 60 is performed by a processor similar to processor 20 shown in FIGS. 1-3 and described above, and, specifically, by an environment module similar to environment module 28 shown in FIG. 1 and described above.

At an operation 62, a determination is made as to whether the patient is asleep or awake. In one embodiment, operation 62 is performed by a processor similar to processor 20 shown in FIGS. 1-3 and described above, and, specifically, by a sleep module similar to sleep module 32 shown in FIG. 1 and described above.

If the patient is determined to be awake at operation 62, then method 52 proceeds to an operation 64, at which breathing cues designed to prompt the patient to breathe at a target breathing rate are determined according to a predetermined algorithm. Determining the breathing cues may include determining a manner in which a feedback system should be controlled to provide the breathing cues to the patient via one or more feedback mechanisms included in the feedback system. The predetermined algorithm may take into account one or more of a user preference, a system default, a physiological function, or an ambient condition in determining the breathing cues. In one embodiment, operation 64 is performed by a processor similar to processor 20 shown in FIGS. 1-3 and described above, and, more particularly, by an algorithm module similar to algorithm module 34 shown in FIG. 1 and described above.

At an operation 66, the breathing cues determined at operation 64 are provided by a feedback system to the patient via one or more feedback mechanisms included in the feedback system. In one embodiment, the feedback system is similar to feedback system 14 shown in FIGS. 1 and 3 and described above, and includes feedback mechanisms similar to feedback mechanisms 26 shown in FIGS. 1 and 3 and described above. The feedback system may be controlled to provide the breathing cues to the patient by a processor similar to processor 20 shown in FIGS. 1-3 and described above, and, more particularly, by a feedback module provided by the processor that is similar to feedback module 36 shown in FIG. 1 and described above.

As was mentioned above, at operation 62 a determination is made as to whether the patient is asleep or awake. If it is determined at operation 62 that the patient is asleep, then method 52 proceeds to an operation 68, at which the provision of breathing cues to the patient according to the predetermined algorithm is ceased. In one embodiment, ceasing the provision of breathing cues according to the predetermined algorithm at operation 68 includes essentially shutting down the feedback system such that any feedback mechanisms included in the feedback system no longer communicate with the patient. In one embodiment, ceasing provision of breathing cues in accordance to the predetermined algorithm at operation 68 includes implementing the feedback system according to a second predetermined algorithm (e.g., as is discussed above with respect to the embodiment illustrated in FIG. 3).

In one embodiment, if method 52 proceeds to operation 68, then function of the system remains at operation 68. In another embodiment, from operation 68, method 52 proceeds back to operation 62 and, if the patient has become awake again, method 52 proceeds on to operation 64.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it should be understood that the present invention contemplates that, to the extent possible, one or more features of any embodiment can be combined with one or more features of any other embodiment.

What is claimed is:

1. A system configured to provide breathing cues to a patient to alleviate insomnia or sleeplessness, the system being configured to provide the breathing cues to the patient as the patient is supported by a support surface, the system comprising:
   a feedback system configured to provide breathing cues to the patient via one or more feedback mechanisms, wherein the feedback system includes multiple feedback mechanisms;
   a patient monitor configured to generate one or more signals that convey information related to one or more physiological functions of the patient, the patient monitor comprising one or more sensors configured to generate one or more signals that convey information related to the one or more physiological functions, wherein the one or more physiological functions of the patient include a current breathing rate; and
   a processor in operative communication with each of the feedback system and the patient monitor, the processor being configured
   (i) to determine information related to at least one of the one or more physiological functions based at least in part on the one or more signals generated by the patient monitor, wherein the determined information includes a target breathing rate,
   (ii) to determine an adjusted target breathing rate based on the current breathing rate and the target breathing rate of the patient, wherein the processor is configured to determine the adjusted target breathing rate to reduce a difference between the current breathing rate and the target breathing rate in an incremental manner,
   (iii) to determine activation and/or deactivation of individual ones of the one or more feedback mechanisms, wherein the determination is based on determined information related to at least one of the one or more physiological functions, and
   (iv) to control the feedback system to activate individual ones of the one or more feedback mechanisms and provide the breathing cues to the patient according to a predetermined algorithm designed to prompt the patient to breathe at the adjusted target breathing rate such that the provided breathing cues correspond to the adjusted target breathing rate and such that the breathing cues are provided by the activated individual ones of the one or more feedback mechanisms, wherein the system further comprises a pressure support apparatus configured to provide a pressurized flow of gas for delivery to an airway of the patient, wherein provided breathing cues by the feedback system include one or more variations of one or more properties of the pressurized flow of gas, wherein the one or more sensors of the patient monitor comprise one or more sensors configured to generate output signals that convey information related to one or more ambient conditions, wherein the processor is further configured to determine one or more ambient conditions based on the generated output signals, wherein the processor is configured such that determination of activation and/or deactivation of individual ones of the one or more feedback mechanisms is further based on the one or more determined ambient conditions, wherein the one or more ambient conditions include one or more of an ambient light level, an ambient noise level, and/or one or more frequency ranges of ambient light, wherein the one or more feedback mechanisms comprise a visual feedback mechanism, wherein the processor is configured to determine activation of the visual feedback mechanism responsive to a determination that the ambient light level is below a light level threshold, wherein the one or more feedback mechanisms further comprise an auditory feedback mechanism, wherein the processor is further configured to determine deactivation of the visual feedback mechanism responsive to a determination that the ambient light level is above a particular light level threshold, and wherein the processor is further configured to determine activation of the auditory feedback mechanism responsive to the determined deactivation of the visual feedback mechanism.

2. A system configured to provide breathing cues to a patient to alleviate insomnia or sleeplessness, the system being configured to provide the breathing cues to the patient as the patient is supported by a support surface, the system comprising:
   a feedback system configured to provide breathing cues to the patient via one or more feedback mechanisms, wherein the feedback system includes multiple feedback mechanisms;
   a patient monitor configured to generate one or more signals that convey information related to one or more physiological functions of the patient, the patient monitor comprising one or more sensors configured to generate one or more signals that convey information related to the one or more physiological functions, wherein the one or more physiological functions of the patient include a current breathing rate; and
   a processor in operative communication with each of the feedback system and the patient monitor, the processor being configured
   (i) to determine information related to at least one of the one or more physiological functions based at least in part on the one or more signals generated by the patient monitor, wherein the determined information includes a target breathing rate,
   (ii) to determine an adjusted target breathing rate based on the current breathing rate and the target breathing rate of the patient, wherein the processor is configured to determine the adjusted target breathing rate to reduce a difference between the current breathing rate and the target breathing rate in an incremental manner,
   (iii) to determine activation and/or deactivation of individual ones of the one or more feedback mechanisms, wherein the determination is based on determined information related to at least one of the one or more physiological functions, and (iv) to control the feedback system to activate individual ones of the one or more feedback mechanisms and provide the breathing cues to the patient according to a predetermined algorithm designed to prompt the patient to breathe at the adjusted target breathing rate such that the provided breathing cues correspond to the adjusted target breathing rate and such that the breathing cues are provided by the activated individual ones of the one or more feedback mechanisms, wherein the system further comprises a pressure support apparatus configured to provide a pressurized flow of gas for delivery to an airway of the patient, wherein provided breathing cues by the feedback system include one or more variations of one or more properties of the pressurized flow of gas, wherein the one or more sensors of the patient monitor comprise one or more sensors configured to generate output signals that convey information related to one or more ambient conditions, wherein the processor is further configured to determine one or more ambient conditions based on the generated output signals, wherein the processor is configured such that determination of activation and/or deactivation of individual ones of the one or more feedback mechanisms is further based on the one or more determined ambient conditions, wherein the one or more ambient conditions include one or more of an ambient light level, an ambient noise level, and/or one or more frequency ranges of ambient light, wherein the one or more feedback mechanisms comprise a visual feedback mechanism, wherein the processor is configured to determine activation of the visual feedback mechanism responsive to a determination that the ambient light level is below a light level threshold, wherein the processor is further configured to determine an effectiveness of the system to alleviate insomnia or sleeplessness for the patient, wherein the effectiveness for the patient is based on an amount of time used to reduce the difference between the current breathing rate and the target breathing rate.

3. The system of claim 2, wherein the one or more physiological functions comprise one or more of a respiration rate, a pulse rate, a pulse rate variability, gross motor activity, or a temperature.

4. The system of claim 2, wherein the determined effectiveness for the patient includes the determination of activation and/or deactivation of individual ones of the one or more feedback mechanisms.

5. A method of providing breathing cues to a patient to alleviate insomnia or sleeplessness, the method being implemented in a system including multiple feedback mechanisms configured to provide breathing cues, the method comprising:

generating one or more signals that convey information related to one or more physiological functions of the patient;

generating output signals that convey information related to one or more ambient conditions;

determining information related to at least one of the one or more physiological functions of the patient based at least in part on the generated one or more signals, wherein the one or more physiological functions of the patient include a current breathing rate;

determining one or more ambient conditions based on the generated output signals;

determining a target breathing rate based on the one or more generated signals;

determining an adjusted target breathing rate based on the current breathing rate and the target breathing rate, wherein the adjusted target breathing rate is determined to reduce a difference between the current breathing rate and the target breathing rate in an incremental manner;

determining activation and/or deactivation of individual ones of the multiple feedback mechanisms, wherein the determination is based on the one or more physiological functions and the one or more determined ambient conditions;

activating individual ones of the multiple feedback mechanisms;

providing breathing cues to the patient via activated individual ones of the multiple feedback mechanisms, the breathing cues being provided according to a predetermined algorithm designed to prompt the patient to breathe at the adjusted target breathing rate such that the provided breathing cues correspond to the adjusted target breathing rate and such that the breathing cues are provided by the activated individual ones of the multiple feedback mechanisms; and providing a pressurized flow of gas for delivery to an airway of the patient;

wherein the provided breathing cues include one or more variations of one or more properties of the pressurized flow of gas, wherein the one or more ambient conditions include an ambient light level, wherein the multiple feedback mechanisms include a visual feedback mechanism, and wherein determining activation and/or deactivation of individual ones of the multiple feedback mechanisms is responsive to a determination that the ambient light level is below a light level threshold, wherein the multiple feedback mechanisms comprise an auditory feedback mechanism, wherein determining deactivation of the visual feedback mechanism is responsive to a determination that the ambient light level is above a particular light level threshold, and wherein a determination of activation of the auditory feedback mechanism is responsive to the determined deactivation of the visual feedback mechanism.

6. A method of providing breathing cues to a patient to alleviate insomnia or sleeplessness, the method being implemented in a system including multiple feedback mechanisms configured to provide breathing cues, the method comprising:

generating one or more signals that convey information related to one or more physiological functions of the patient;

generating output signals that convey information related to one or more ambient conditions;

determining information related to at least one of the one or more physiological functions of the patient based at least in part on the generated one or more signals, wherein the one or more physiological functions of the patient include a current breathing rate;

determining one or more ambient conditions based on the generated output signals;

determining a target breathing rate based on the one or more generated signals;

determining an adjusted target breathing rate based on the current breathing rate and the target breathing rate, wherein the adjusted target breathing rate is determined to reduce a difference between the current breathing rate and the target breathing rate in an incremental manner;

determining activation and/or deactivation of individual ones of the multiple feedback mechanisms, wherein the determination is based on the one or more physiological functions and the one or more determined ambient conditions;

activating individual ones of the multiple feedback mechanisms;

providing breathing cues to the patient via activated individual ones of the multiple feedback mechanisms, the breathing cues being provided according to a predetermined algorithm designed to prompt the patient to breathe at the adjusted target breathing rate such that the provided breathing cues correspond to the adjusted target breathing rate and such that the breathing cues are provided by the activated individual ones of the multiple feedback mechanisms; and providing a pressurized flow of gas for delivery to an airway of the patient;

wherein the provided breathing cues include one or more variations of one or more properties of the pressurized flow of gas, wherein the one or more ambient conditions include an ambient light level, wherein the multiple feedback mechanisms include a visual feedback mechanism, and wherein determining activation and/or deactivation of individual ones of the multiple feedback mechanisms is responsive to a determination that the ambient light level is below a light level threshold, further comprising:

determining an effectiveness of the method to alleviate insomnia or sleeplessness for the patient, wherein the effectiveness for the patient is based on an amount of time used to reduce the difference between the current breathing rate and the target breathing rate.

7. The method of claim 6, wherein the determined effectiveness for the patient includes the determination of activation and/or deactivation of individual ones of the multiple feedback mechanisms.

8. The method of claim 7, wherein metrics of the determined effectiveness for the patient are stored on an electronic storage medium and used to provide subsequent treatments.

9. The method of claim 6, wherein the one or more physiological functions comprise one or more of a respiration rate, a pulse rate, a pulse rate variability, gross motor activity, or a temperature.

10. A system configured to provide breathing cues to a patient to alleviate insomnia or sleeplessness, the system comprising:

means for providing breathing cues to the patient via one or more feedback mechanisms, wherein the means for providing breathing cues includes multiple feedback mechanisms;

means for generating one or more signals that convey information related to one or more physiological functions of the patient;

means for generating output signals that convey information related to one or more ambient conditions;

means for determining information related to at least one of the one or more physiological functions of the patient based at least in part on the generated one or more signals, wherein the one or more physiological functions of the patient include a current breathing rate;

means for determining one or more ambient conditions based on the generated output signals;

means for determining a target breathing rate based on the one or more generated output signals;

means for determining an adjusted target breathing rate based on the current breathing rate and the target breathing rate, wherein the adjusted target breathing rate is determined to reduce a difference between the current breathing rate and the target breathing rate in an incremental manner;

means for determining activation and/or deactivation of individual ones of the multiple feedback mechanisms, wherein the determination is based on the one or more physiological functions and the one or more determined ambient conditions;

means for activating individual ones of the multiple feedback mechanisms;

means for providing breathing cues via activated individual ones of the multiple feedback mechanisms, the breathing cues being provided according to a predetermined algorithm designed to prompt the patient to breathe at the adjusted target breathing rate such that the provided breathing cues correspond to the adjusted target breathing rate and such that the breathing cues are provided by the activated individual ones of the multiple feedback mechanisms; and means for providing a pressurized flow of gas for delivery to an airway of the patient, wherein the provided breathing cues include one or more variations of one or more properties of the pressurized flow of gas, wherein the one or more ambient conditions include an ambient light level, wherein the multiple feedback mechanisms include a visual feedback mechanism, and wherein operation of the means for determining activation and/or deactivation of individual ones of the multiple feedback mechanisms is responsive to a determination that the ambient light level is below a light level threshold, wherein the multiple feedback mechanisms comprise an auditory feedback mechanism, wherein the means for determining activation and/or deactivation of individual ones of the multiple feedback mechanisms is configured to determine deactivation of the visual feedback mechanism responsive to a determination that the ambient light level is above a particular light level threshold, and further configured to determine activation of the auditory feedback mechanism responsive to the determined deactivation of the visual feedback mechanism.

11. A system configured to provide breathing cues to a patient to alleviate insomnia or sleeplessness, the system comprising:

means for providing breathing cues to the patient via one or more feedback mechanisms, wherein the means for providing breathing cues includes multiple feedback mechanisms;

means for generating one or more signals that convey information related to one or more physiological functions of the patient;

means for generating output signals that convey information related to one or more ambient conditions;

means for determining information related to at least one of the one or more physiological functions of the patient based at least in part on the generated one or more signals wherein the one or more physiological functions of the patient include a current breathing rate;

means for determining one or more ambient conditions based on the generated output signals;

means for determining a target breathing rate based on the one or more generated output signals;

means for determining an adjusted target breathing rate based on the current breathing rate and the target breathing rate, wherein the adjusted target breathing rate is determined to reduce a difference between the current breathing rate and the target breathing rate in an incremental manner;

means for determining activation and/or deactivation of individual ones of the multiple feedback mechanisms, wherein the determination is based on the one or more physiological functions and the one or more determined ambient conditions;

means for activating individual ones of the multiple feedback mechanisms;

means for providing breathing cues via activated individual ones of the multiple feedback mechanisms, the breathing cues being provided according to a predetermined algorithm designed to prompt the patient to breathe at the adjusted target breathing rate such that the provided breathing cues correspond to the adjusted target breathing rate and such that the breathing cues are provided by the activated individual ones of the multiple feedback mechanisms; and means for providing a pressurized flow of gas for delivery to an airway of the patient, wherein the provided breathing cues include one or more variations of one or more properties of the pressurized flow of gas, wherein the one or more ambient conditions include an ambient light level, wherein the multiple feedback mechanisms include a visual feedback mechanism, and wherein operation of the means for determining activation and/or deactivation of individual ones of the multiple feedback mechanisms is responsive to a determination that the ambient light level is below a light level threshold, further comprising:

means for determining an effectiveness of the system to alleviate insomnia or sleeplessness for the patient, wherein the effectiveness for the patient is based on the amount of time used to reduce the difference between the current breathing rate and the target breathing rate.

12. The system of claim 11, wherein the determined effectiveness for the patient includes the determination of activation and/or deactivation of individual ones of the multiple feedback mechanisms.

13. The system of claim 12, wherein the one or more physiological functions comprise one or more of a respiration rate, a pulse rate, a pulse rate variability, gross motor activity, or a temperature.

14. The system of claim 12, wherein metrics of the determined effectiveness for the patient are stored on an electronic storage medium and used to provide subsequent treatments.

* * * * *